(12) United States Patent
Del Medico

(10) Patent No.: US 11,324,540 B2
(45) Date of Patent: May 10, 2022

(54) DEVICE FOR THE CERCLAGE OF FRACTURED BONES AND SYSTEM FOR THE CERCLAGE OF FRACTURED BONES COMPRISING SUCH DEVICE

(71) Applicant: Nilli Del Medico, Orbassano (IT)

(72) Inventor: Nilli Del Medico, Orbassano (IT)

( * ) Notice: Subject to any disclaimer, the term of this patent is extended or adjusted under 35 U.S.C. 154(b) by 0 days.

(21) Appl. No.: 17/277,374

(22) PCT Filed: Sep. 26, 2019

(86) PCT No.: PCT/IB2019/058178
§ 371 (c)(1),
(2) Date: Mar. 18, 2021

(87) PCT Pub. No.: WO2020/070596
PCT Pub. Date: Apr. 9, 2020

(65) Prior Publication Data
US 2021/0307799 A1    Oct. 7, 2021

(30) Foreign Application Priority Data

Oct. 1, 2018  (IT) .......................... 102018000009065

(51) Int. Cl.
*A61B 17/82*    (2006.01)
*A61B 17/80*    (2006.01)

(52) U.S. Cl.
CPC ............ *A61B 17/82* (2013.01); *A61B 17/809* (2013.01); *A61B 17/8085* (2013.01)

(58) Field of Classification Search
CPC .............. A61B 17/809; A61B 17/8028; A61B 17/8085; A61B 17/82
See application file for complete search history.

(56) References Cited

U.S. PATENT DOCUMENTS

| 5,190,545 A | * | 3/1993 | Corsi | ..................... A61B 17/82 606/309 |
| 5,415,658 A | | 5/1995 | Kilpela et al. | |

(Continued)

FOREIGN PATENT DOCUMENTS

| CN | 204306889 U | 5/2015 |
| DE | 102015120847 A1 | 6/2017 |

(Continued)

OTHER PUBLICATIONS

International Search Report and Written Opinion of the International Searching Authority dated Jan. 28, 2020 for International Patent Application No. PCT/IB2019/058178.

*Primary Examiner* — David W Bates
(74) *Attorney, Agent, or Firm* — Howson & Howson LLP

(57) ABSTRACT

A device for the cerclage of fractured bone as well as to a cerclage system using such device are provided. The cerclage device comprises a cerclage wire or thread and at least one spacer arranged on the cerclage wire or thread. The at least one spacer is made as a band having a substantially rectangular plan and a concave profile. Owing to the concave profile, the band can adapt to the surface of the fractured bone; in addition, the force exerted on the bone by the cerclage wire is advantageously distributed over the entire surface of the band. The cerclage device further comprises at least one safety thread which allows preventing the spacer from becoming lost in the patient's body in case the cerclage wire or thread tears off.

20 Claims, 9 Drawing Sheets

(56) References Cited

U.S. PATENT DOCUMENTS

| | | | |
|---|---|---|---|
| 5,665,089 A * | 9/1997 | Dall | A61B 17/82 606/71 |
| 5,993,452 A * | 11/1999 | Vandewalle | A61B 17/82 606/103 |
| 7,250,054 B2 | 7/2007 | Allen et al. | |
| 7,255,701 B2 | 8/2007 | Allen et al. | |
| 9,333,021 B2 | 5/2016 | Gephart | |
| 9,561,064 B2 | 2/2017 | Goodwin et al. | |
| 9,693,812 B2 | 7/2017 | Zeetser et al. | |
| 10,426,532 B2 | 10/2019 | Goodwin et al. | |
| 10,835,301 B1 * | 11/2020 | Paranjpe | A61B 17/8009 |
| 2004/0087954 A1 | 5/2004 | Allen et al. | |
| 2006/0058795 A1 * | 3/2006 | Boyd | A61B 17/82 606/281 |
| 2006/0122623 A1 | 6/2006 | Truckai et al. | |
| 2010/0274249 A1 | 10/2010 | Fernandez | |
| 2013/0289564 A1 * | 10/2013 | Bernstein | A61B 17/82 606/74 |
| 2014/0243901 A1 * | 8/2014 | Mebarak | A61B 17/809 606/281 |
| 2017/0181780 A1 | 6/2017 | Cremer et al. | |
| 2018/0161083 A1 * | 6/2018 | Kobayashi | A61B 17/82 |

FOREIGN PATENT DOCUMENTS

| | | | |
|---|---|---|---|
| WO | 2012007910 A1 | 1/2012 | |
| WO | WO-2012007910 A1 * | 1/2012 | A61B 17/82 |

* cited by examiner

DEVICE FOR THE CERCLAGE OF FRACTURED BONES AND SYSTEM FOR THE CERCLAGE OF FRACTURED BONES COMPRISING SUCH DEVICE

TECHNICAL FIELD

The present invention refers to a device for the cerclage of fractured bones.

The present invention also refers to a system for the cerclage of fractured bones which uses said cerclage device.

PRIOR ART

In the field of orthopedic surgery, the use of cerclage wires is known in the case of very serious fractures or in bone reconstruction procedures. Such cerclage wires are implanted in a permanent manner in order to keep the bone portions together.

In particular, the object of said cerclage wires is to apply a circumferential compression force to the bone portions; to reach such object, the cerclage wire is tightened around the bone and then locked.

Generally, said wires are metal wires, even if the use of wires made of plastic material is known.

A cerclage wire is illustrated, for example, in U.S. Pat. No. 5,993,452.

Also known are cerclage systems that comprise a plate arranged on the bone and a plurality of cerclage wires for maintaining said plate tightly coupled to the bone.

In this respect, with reference to FIG. 1A, a cerclage system 100 of known type is illustrated, applied to a fractured bone, in particular to a femur having a trochanteric fracture. The cerclage system 100 comprises an osteosynthesis plate 101 abutting against the bone and a plurality of cerclage wires 103 wound around the fractured femur and tightened thereon, in a manner so as to keep the plate 101 coupled and in close contact with said femur. For such purpose, the plate 101 provides for a plurality of seats 105, and a corresponding cerclage wire 103 passes through each of such seats.

An analogous cerclage system is known, for example, from US 2006/0058795.

A major drawback of the known cerclage wires is linked to the risk of onset of bone tissue necrosis at the zone in contact with the cerclage wires.

Such risk is due to the fact that the cerclage wires must be firmly tightened on the bone in order to effectively keep the bone portions together or the bone and the osteosynthesis plate together; the high pressure exerted by the cerclage wires on the bone can lead to insufficient blood circulation in the bone tissue, and to consequent necrosis.

In order to remedy such drawback, cerclage devices have recently been developed comprising a cerclage wire or thread and a plurality of spacers, arranged on said wire or thread at a certain distance from each other, such to reduce the extension of the contact zones between said wire or thread and the bone to which it is applied: in such a manner, the risk of onset of necrosis is reduced.

With reference to FIG. 1B, a cerclage system 200 is illustrated, achieved as follows: said system comprises an osteosynthesis plate 201 provided with seats 205 for housing corresponding cerclage devices 210; each of said cerclage devices 210 in turn comprises a wire 203 and a plurality of spacers 207 arranged on said wire 3, which allow maintaining the wire 3 at a certain distance from the bone to which the system 200 is applied. The spacers 207 are obtained in a manner so that they can slide along the wire 203 and the cerclage device 1 also comprises locking means suitable for preventing such sliding, such to be able to fix said spacers 207 in the desired position. Both the wire 203 and the spacers 207 are made of materials suitable for surgical use.

A cerclage system of the kind illustrated in FIG. 1B is known, for example, from document US 2006/0122623, as well as from document WO 2012/007910.

A cerclage system of this type, even if it has proven its ability to avoid the risk of necrosis, is not drawback-free and it is certainly susceptible of improvements.

More particularly, both in US 2006/0122623 and WO 2012/007910 the spacers are made as spheres or cylinders and—because of the convex surface of said spacers—the contact surface between each spacer and the bone surface is very small, even point-like in the case of spherical spacers.

As a result, the compression force applied to the bone by the cerclage wire is concentrated in a reduced number of points, with values of the exerted pressure that are therefore very high.

In addition, still because of the convex surface of the spacers, any rubbing of these spacers might damage the bone surface, thus increasing the invasiveness of the cerclage system.

The main object of the present invention is to provide an improved cerclage device and a cerclage system that allow eliminating or at least minimizing the aforementioned drawbacks.

These and other objects are achieved by means of a cerclage device and a cerclage system as claimed in the appended claims.

SUMMARY OF THE INVENTION

According to the invention, the device for the cerclage of a fractured bone comprises a cerclage wire or thread and at least one spacer arranged on said wire or thread, wherein said at least one spacer is made as a band having a substantially rectangular plan and a concave profile.

By virtue of the fact that the force exerted on the bone by the cerclage wire is advantageously distributed over the entire surface of the band, the pressure exerted on the fractured bone is remarkably lower than that of prior art cerclage devices.

Owing to the concave profile, the band can advantageously adapt to the profile of the surface of the fractured bone.

In an embodiment of the invention, the band is preformed so as to have a concave profile corresponding to the profile of the bone for which it is intended.

In an alternative embodiment of the invention, the band is made of a deformable material and the concave profile is conferred to the band during the application thereof, whereby said concave profile can be accurately adapted to the profile of said bone.

Said band can be made of any materials suitable for surgical use.

More particularly, said band can be made of a suitable metal or of a suitable plastic material such as, for example, polyethylene.

According to the invention, the band comprises a body having a substantially rectangular plan and a pair of bent end walls, each of said end walls being provided with a throughhole for the passage of the cerclage wire or thread therethrough.

Said end walls are bent—preferably at an angle of about 90°—so as to extend away from the face of the band that, in use, is intended to be in contact with the fractured bone.

According to the invention, the cerclage device, in addition to the cerclage wire on which the spacer is arranged, comprises one or more safety threads, and each of said end walls is provided, in addition to the through-hole for the passage of the cerclage wire or thread therethrough, with one or more additional through-holes for the passage of corresponding safety threads therethrough.

Thanks to this measure, even if the cerclage wire or thread should tear off, the band is kept secured to said one or more safety threads, whereby it cannot become lost in the patient's body.

In a preferred embodiment of the invention, the through-holes for the passage of the cerclage wire or thread therethrough are closed, i.e. they are entirely contained within the corresponding end wall, and they preferably have a circular profile.

In an alternative embodiment of the invention, the through-holes for the passage of the cerclage wire or thread therethrough may also be open upwards, i.e. they may open on a face of the end wall that is farthest from the face of the band that, in use, is intended to be in contact with the bone.

The additional through-holes of the passage of the safety thread(s) therethrough are in any case preferably closed through-holes.

In a preferred embodiment of the invention, the face of the band that, in use, is intended to be in contact with the fractured bone is smooth.

According to this embodiment, thanks to the smooth, concave surface of the band face, any risk of rubbing against the bone surface and of consequent bone damage is advantageously avoided.

In another preferred embodiment of the invention, the face of the band that, in use, is intended to be in contact with the fractured bone is provided with projecting teeth oriented towards the surface of said bone.

According to this embodiment, owing to the provision of the projecting teeth, the stability of positioning of the band is improved.

In this embodiment, said projecting teeth can be attached to the plate body, or they can be obtained directly therefrom by bending corresponding portions of said body.

Still according to the invention, one or more cerclage devices of the kind described above can be associated with an osteosynthesis plate in order to form a cerclage system allowing firm and effective retainment of said plate against the fractured bone.

BRIEF DESCRIPTION OF THE DRAWINGS

Additional features and advantages of the invention will be evident to the person skilled in the art starting from the ensuing detailed description of some preferred embodiments of the invention, provided by way of non-limiting example, with reference to the attached drawings, in which.

DESCRIPTION OF PREFERRED EMBODIMENTS OF THE INVENTION

Figure 1A:
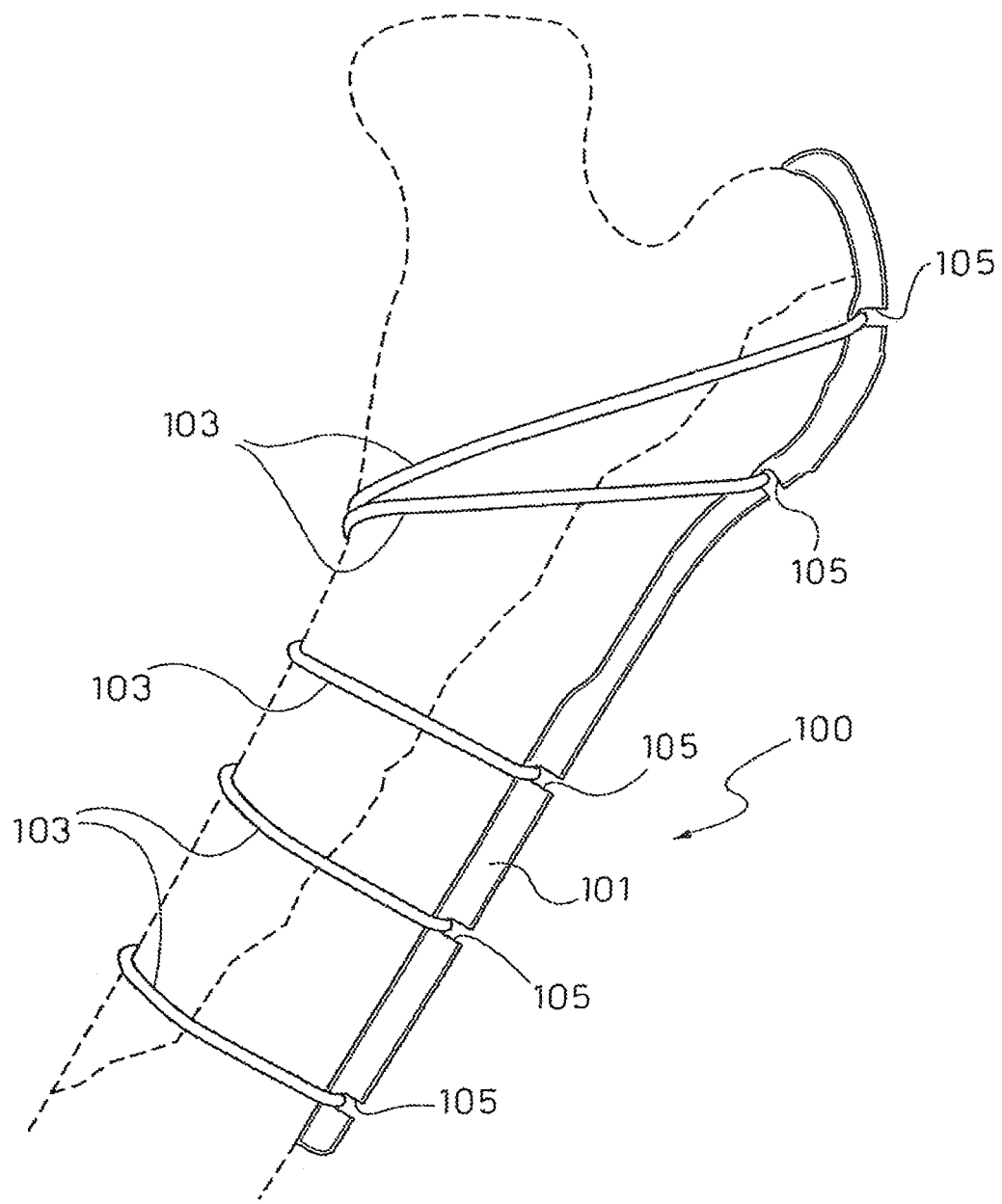
FIGS. 1A and 1B illustrate cerclage systems of known type for fractured bones.
Figure 1B:
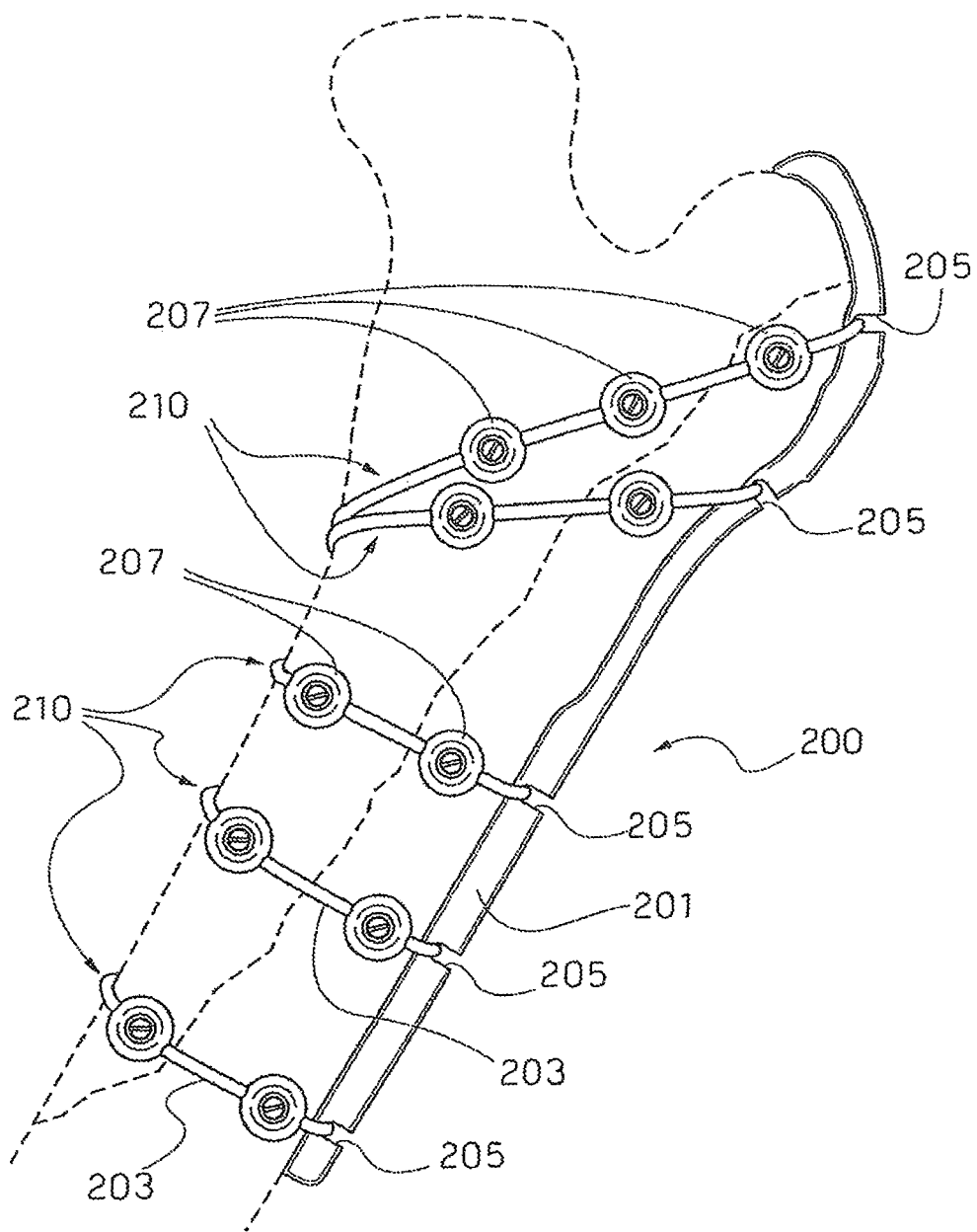
Figure 2:
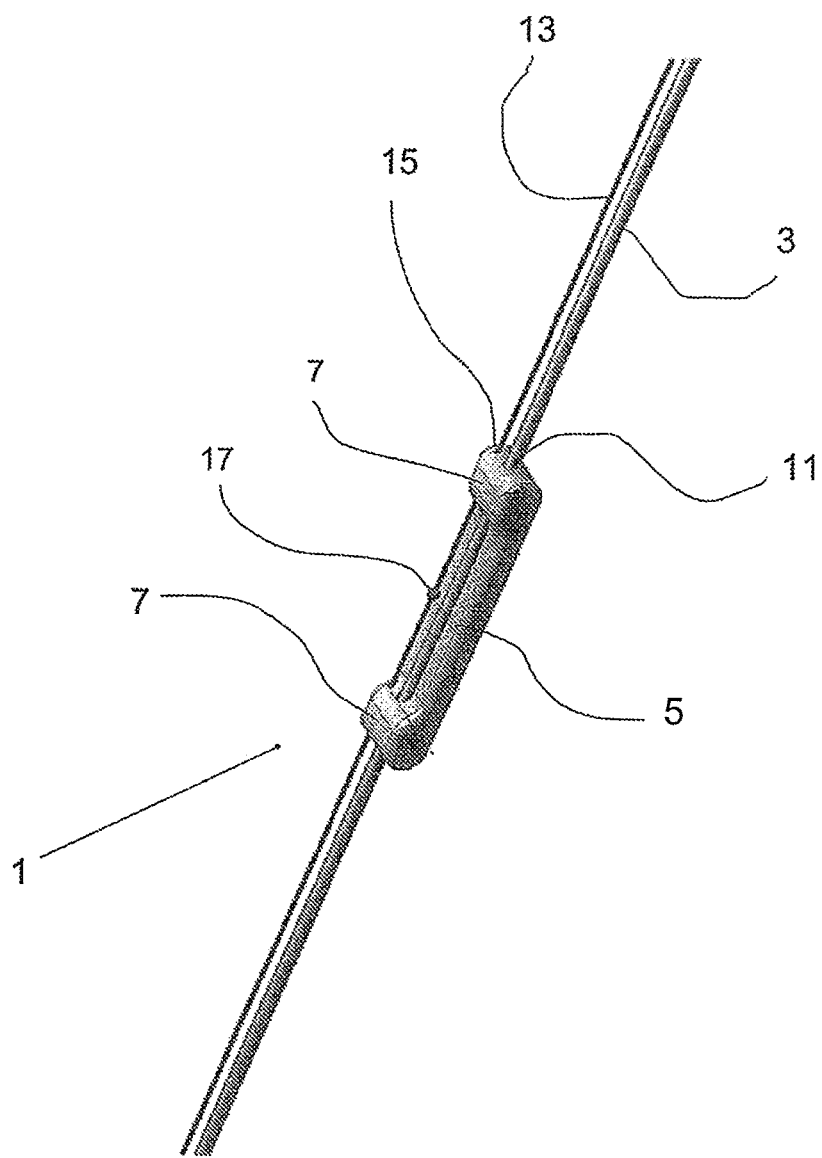
FIG. 2 shows a cerclage device for fractured bones according to a first embodiment of the invention.
Figure 3:
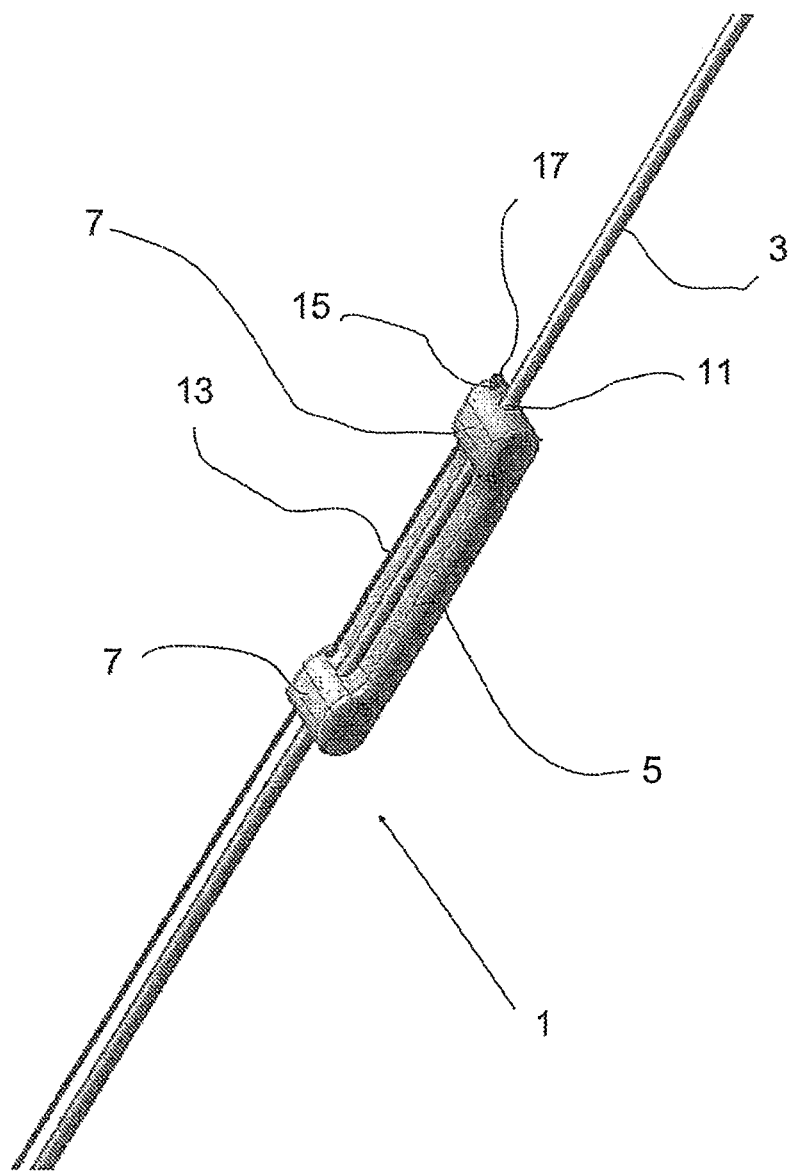
FIG. 3 shows a cerclage device for fractured bones according to a first variant of the first embodiment of the invention.
Figure 4:
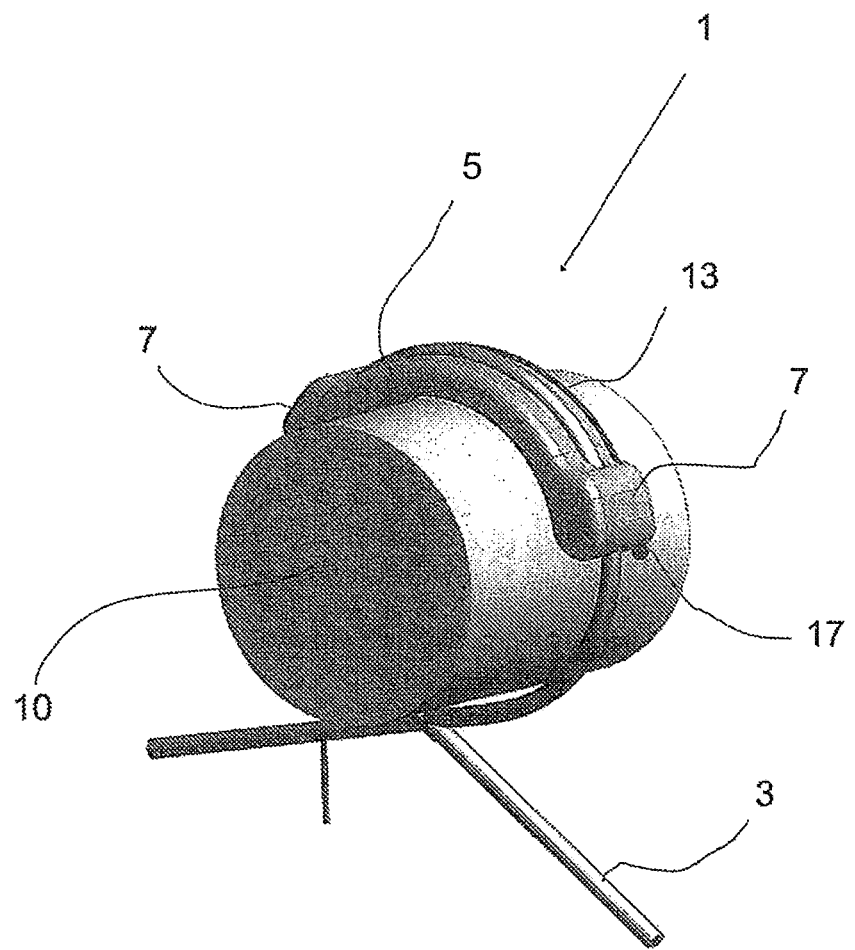
FIG. 4 schematically shows the cerclage of FIG. 3 applied to a fractured bone.

Referring to FIGS. 2-4, there is schematically illustrated a device 1 for the cerclage of a fractured bone 10 according to a first preferred embodiment of the invention.

The cerclage device 1 comprises a cerclage wire 3 and at least one spacer 5 arranged on said cerclage wire 3, said spacer 5 allowing maintaining the cerclage wire 3 at a certain distance from the bone to which the cerclage device 1 is applied, once the cerclage wire is tightened and locked on said bone.

According to the invention, the spacer is made as a band 5 having a substantially rectangular plan and a concave profile.

Thanks to this measure, the force exerted on the fracture bone by the cerclage device 1 is distributed over the entire surface of the band 5.

The band 5 can be made of any material suitable for surgical use, preferably a metal suitable for surgical use or a plastic material suitable for surgical use.

If the band 5 is made of a rigid material, it can be preformed in order to have the desired concave profile.

In the embodiment shown in FIGS. 2-4, the band 5 is made of a material flexible enough to be capable of being deformed for being adapted to the profile of the bone to which the cerclage device 1 is applied (see FIG. 4).

For example, in the embodiment shown in FIGS. 2-4, the band 5 can be made of polyethylene.

Advantageously, owing to the fact that the band 5 has a profile such that it can be adapted to the fractured bone to which the cerclage device 1 is applied, said band will tend to maintain the position assigned thereto and not to move relative to said bone.

As a result, it would be possible to avoid use of dedicated means for locking said band 5 in its desired position (even if said means can however be provided).

In the embodiment illustrated in FIGS. 2-4, the face of the band that, in use, is intended to be in contact with the surface of the fractured bone is smooth.

Thanks to this measure, any risks of rubbing and damaging of the surface of the bone to which the band 5 is applied are avoided.

According to the invention, the band 5 has a pair of end walls 7 that are bent—more particularly, preferably bent at about 90°—and extend in a direction opposite to the face of the band that, in use, is intended to be in contact with the surface of the fractured bone, and each of the end walls 7 is provided with a through-hole 11 for the passage of the cerclage wire 3 therethrough.

Still according to the invention, the cerclage device 1, in addition to the cerclage wire 3 on which the band 5 is arranged, comprises a safety thread 13 and, correspondingly, each end wall 7 of the band 5 is provided with an additional through-hole 15 for said safety thread 13.

A stop element 17 is arranged on said safety thread 13, which stop element has a size larger than the size of the additional through-holes 15 of the end walls 17, whereby it cannot pass therethrough and, consequently, the safety thread cannot be removed from the band 5.

The stop element 17 can be provided at an intermediate position of said safety thread 13, between the two end walls 7 of the band 5 (see FIG. 2), or at an end of the safety thread 13 (see the variant of FIG. 3).

Thanks to the safety thread 13, even if the cerclage wire 3 tears off, the band 5 does not risk to become lost in the patient's body.

Advantageously, the additional through-holes 15 have a diameter slightly larger than the diameter of the safety thread 13, such that said safety wire or thread is not subjected to any friction or rubbing and therefore it is not subject to wear. In addition, the safety thread 13 has a length such to be untensioned during normal use of the cerclage device 1, so as not to be subjected to any stresses during said normal use.

In a known and not illustrated manner, one or more cerclage devices 1 of the type described above can be associated with an osteosynthesis plate for forming a cerclage system allowing firm and effective retainment of said plate against the fractured bone, without any risks for the patient.

Figure 5:
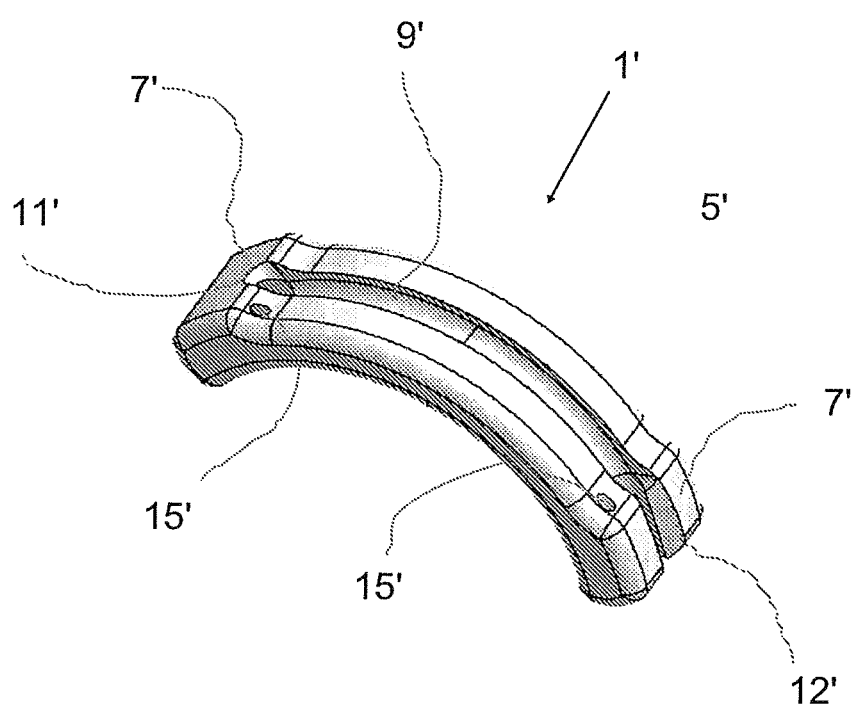
FIG. 5 shows a cerclage device for fractured bones according to a second variant of the first embodiment of the invention.

FIG. 5 illustrates a further variant of the cerclage device of FIGS. 2-4. In this variant, too, the cerclage device 1' comprises a spacer 5' in the form of a band, provided with a pair of end walls 7' bent in a direction opposite to the face of the band that, in use, is intended to be in contact with the surface of the fractured bone, said end walls being provided with corresponding through-holes 11', 12' for the passage of the cerclage wire (not shown) therethrough.

In this variant, one of the end walls 7' has a through-hole 11' which is "closed", i.e. which is entirely contained within the corresponding end wall; in particular, said through-hole 11' has a circular profile. The other end wall, instead, has a through-hole 12' which is open upwards, i.e. which opens on the face of the end wall 7' opposite to the face of the band 5' that, in use, is intended to be in contact with the bone.

The through-hole 12' has substantially the shape of a lying down "C" and has converging upper edges arranged to retain the cerclage wire.

As can be seen in FIG. 5, the additional through-holes 15' in any case preferably "closed" through-holes, with a substantially circular profile.

Figure 6:
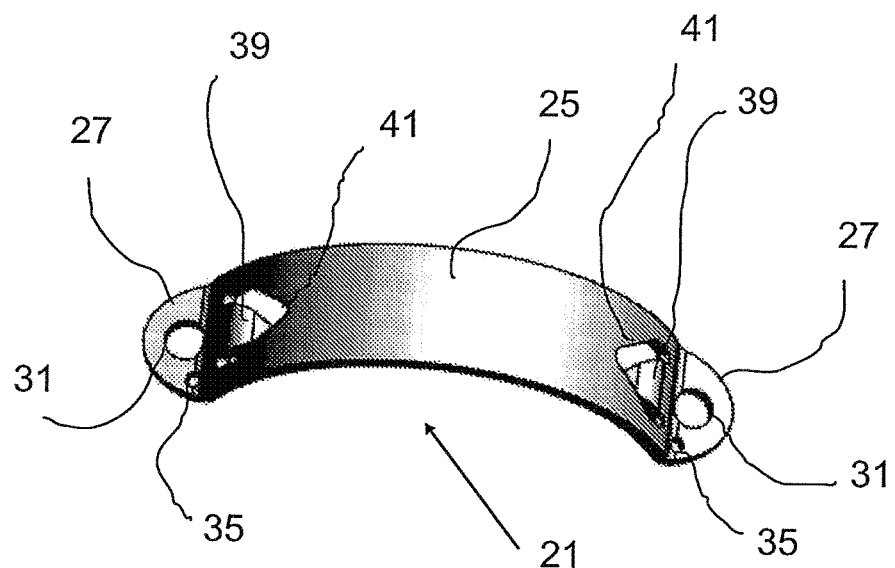
FIG. 6 shows a cerclage device for fractured bones according to a second embodiment of the invention.

Turning now to FIG. 6, there is shown a second preferred embodiment of the invention.

In this embodiment, too, the cerclage device 21 comprises a cerclage wire and at least one spacer 25 arranged on said cerclage wire, said spacer being made as a band 25 having a substantially rectangular plan and a concave profile.

In the embodiment of FIG. 6, said ban 25 is made of a metal suitable for surgical use.

The embodiment of FIG. 6 differs from the first embodiment described above in that the face of the band that, in use, is intended to be in contact with the surface of the fractured bone is provided with teeth 39 projecting from the body of the band 5 in a direction opposite to the end walls 27 of the band, i.e. towards the surface of the fractured bone when the cerclage device 1 is in use.

The teeth 39 might be attached to the surface of the body of the band 25.

However, in the illustrated embodiment, said teeth are obtained directly from the body of said band, by making cuts 41 and bending the portions of the band body thus separated from the rest of said band body.

The teeth 39, in use, contribute to increase the stability of positioning of the band 25 on the fractured bone.

In this embodiment, too, the end walls 27 of the band 25 are provided each with a through-hole 31 for the passage of the cerclage wire therethrough and with one or more additional through-holes 35 for the passage of the safety thread therethrough.

Figure 7:
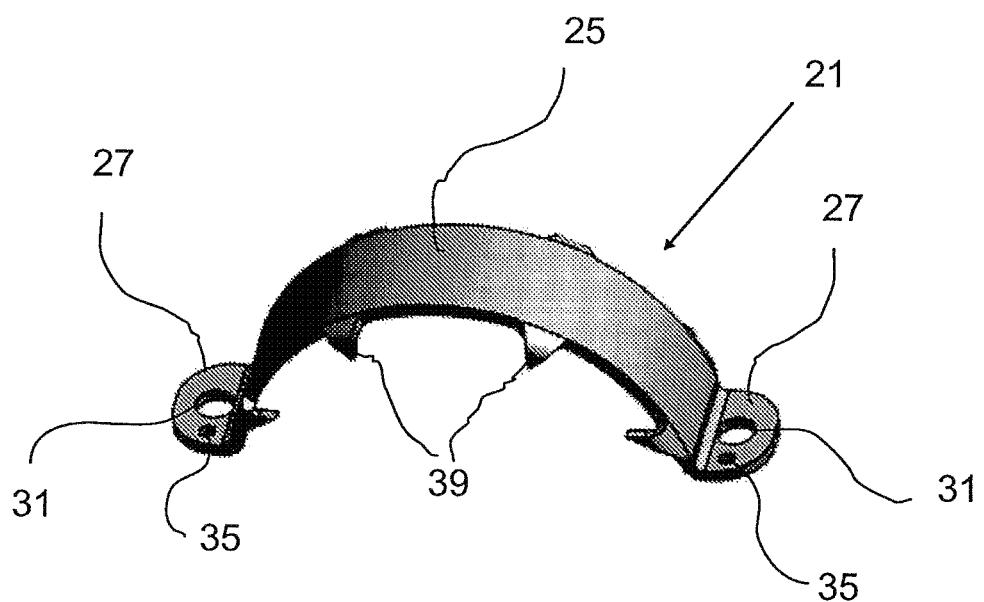
FIG. 7 shows a cerclage device for fractured hones according to a first variant of the second embodiment of the invention.
Figure 8:
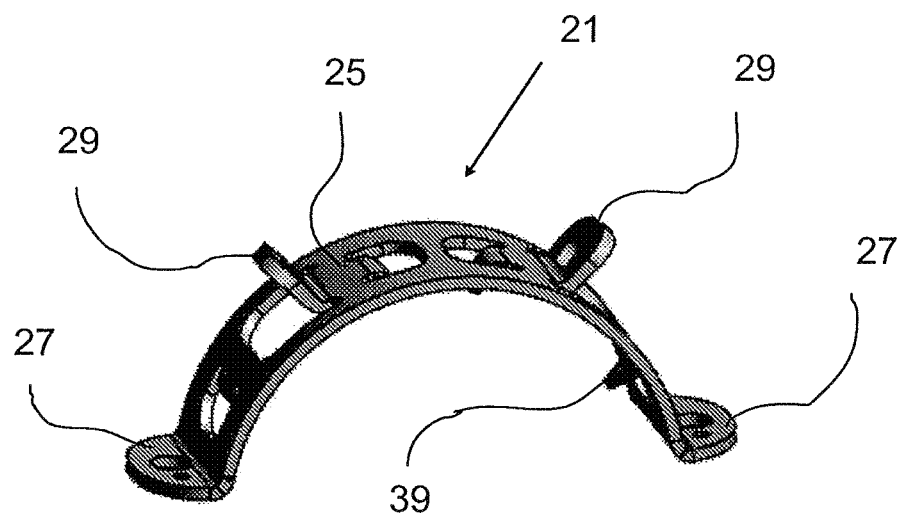
FIG. 8 shows a cerclage device for fractured bones according to a second variant of the second embodiment of the invention.
Figure 9:
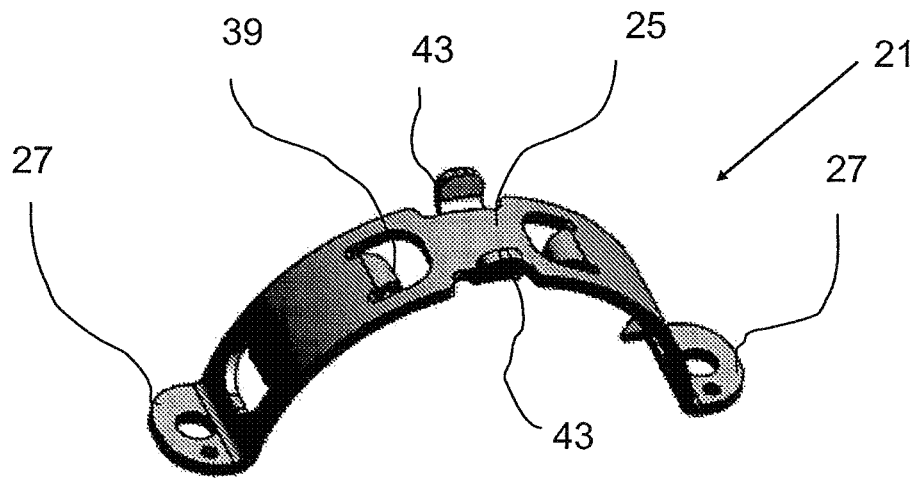
FIG. 9 shows a cerclage device for fractured bones according to a third variant of the second embodiment of the invention.

FIGS. 7-9 show respective variants of the second preferred embodiment of the invention of FIG. 5.

In the variant of FIG. 7, the teeth 39 are not obtained by means of cuts in the body of the band 25, but they are arranged along the perimeter of said body.

The teeth 39 can be made integral with the body of the band 25 and then suitably bent.

In the variant of FIG. 8, the band 25 comprises, in addition to the end walls 27, one or more intermediate walls 29 (two in the illustrated example).

Also the intermediate walls 29 extend in a direction opposite to the face of the band that, in use, is intended to be in contact with the surface of the fractured bone, and each of the intermediate walls 29 is provided with a through-hole for the passage of the cerclage wire therethrough, and with one or more additional through-holes for corresponding safety threads.

Said end walls allow guiding the cerclage wire and the safety thread so that they extend substantially parallel to the longitudinal axis of the body of the band 25.

The intermediate walls 29 might be attached to the surface of the body of the band 25.

However, in the illustrated embodiment, they are obtained directly from the body of said band, by making cuts and bending the portions of the band body thus separated from the rest of said band body.

In the variant of FIG. 9, in order to guide the cerclage wire and the safety thread so that they extend substantially parallel to the longitudinal axis of the body of the band 25, there are provided, instead of the intermediate walls of the previous variant, two lateral bent tabs 43, which extend on opposite sides of the body of the band 25 in a direction opposite to the face of said band that, in use, is intended to be in contact with the surface of the fractured bone.

Said lateral tabs 43 are preferably made integral with the body of the band 25 and then suitably bent.

Figure 10:
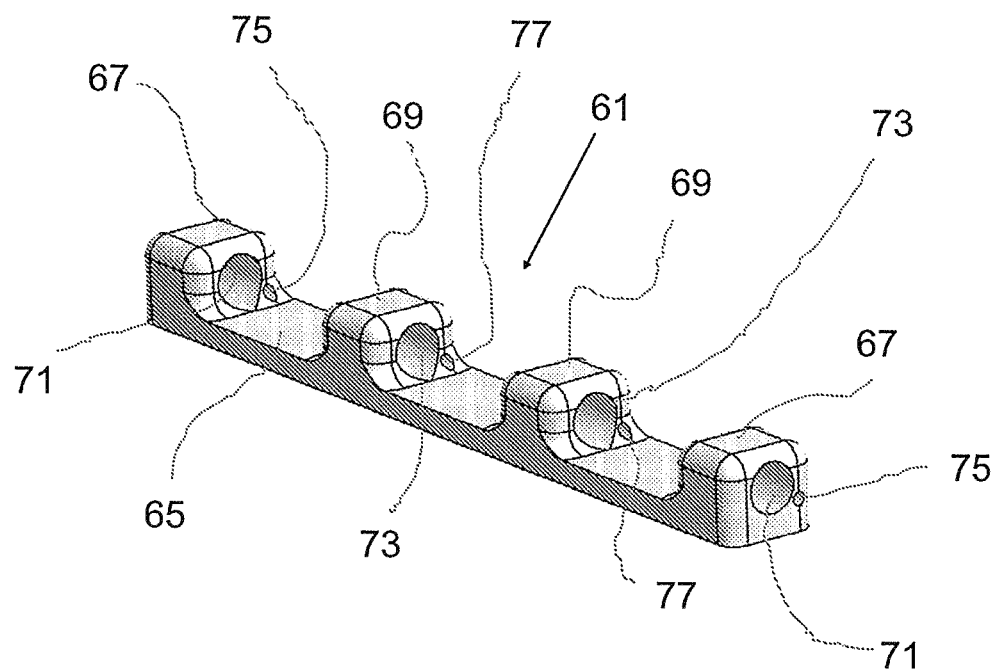
FIG. 10 shows a cerclage device for fractured bones according to a third embodiment of the invention.

Turning now to FIG. 10, this illustrates a third preferred embodiment of the invention.

In this embodiment, too, the cerclage device 61 comprises a cerclage wire and at least one spacer 65 made as band having a substantially rectangular plan and a concave profile.

The cerclage device of this embodiment, like the one of the embodiment previously described, further comprises, in addition to the end walls 67 provided with corresponding through-holes 71 for the passage of the cerclage wire of the band therethrough, intermediate walls 69, these, too, being provided with corresponding through-holes 73 for the passage of the cerclage wire of the band therethrough.

In this embodiment, too, the end walls 67 and the intermediate walls 69 are further provided with corresponding additional through-holes 75, 77 for the passage of a safety thread therethrough.

The embodiment of FIG. 10 differs from the previous embodiment in that the face of the band that, in use, is intended to be in contact with the surface of the fractured bone is smooth, like that of the embodiment shown in FIGS. 2-4.

In addition, according to this embodiment, the band 65 is not preformed with a certain concave profile, but it has a substantially flat profile. Said band can subsequently be deformed to obtain, each time, the desired concave profile for the specific application.

Figure 11:
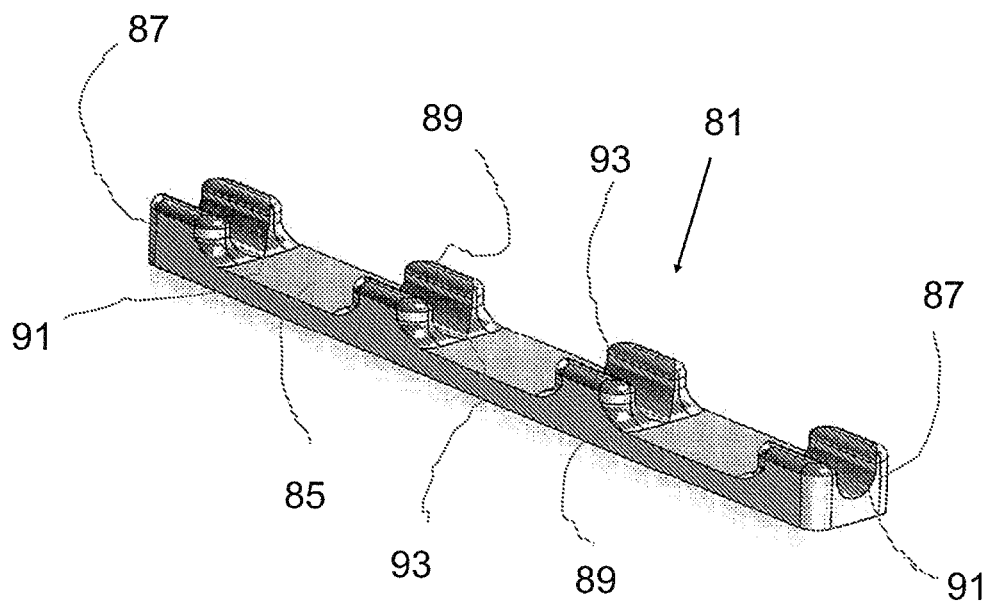
FIG. 11 shows a cerclage device for fractured bones according to a fourth embodiment of the invention.

Turning now to FIG. 11, there is illustrated a fourth preferred embodiment of the invention.

In this embodiment, too, the cerclage device 81 comprises a cerclage wire and at least one spacer 85 made as a band having a substantially rectangular plan and a concave profile.

The cerclage device of this embodiment, like the one of the previously described embodiment, further comprises, in addition to the end walls 87 provided with the corresponding through-holes 91 for the passage of the cerclage wire of the band therethrough, intermediate walls 89, these, too, being provided with corresponding through-holes 93 for the passage of the cerclage wire of the band therethrough.

In this embodiment, too, the face of the band that, in use, is intended to be in contact with the surface of the fractured bone is smooth and has a flat profile, which can subsequently be deformed to obtain each time a desired concave profile for the specific application.

The embodiment of FIG. 11 differs from the previously described embodiment in that the through-holes 91, 93 provided in the end walls 87 and in the intermediate walls 89, respectively, are not closed, but open upwards, i.e. towards the face of the relevant end wall or intermediate wall opposite to the face of the band that, in use, is intended to be in contact with the surface of the bone.

The through-holes 91, 93 have substantially the shape of a lying down "C" and have converging upper edges arranged to retain the cerclage wire.

In this embodiment, too, the additional through-holes (even if not shown) for the safety wire(s) are, however, preferably "closed" through-holes having a substantially circular profile.

Generally, it is evident that the foregoing detailed description of some preferred embodiments of the invention has been provided by way of non-limiting example and that several variants and modifications are possible without departing from the scope of protection of the present invention as defined in the appended claims.

For example, although the illustrated embodiments refer to a device comprising a cerclage wire, it is evident that said wire might be replaced with a cerclage thread.

The invention claimed is:

1. A cerclage device for the cerclage of a fractured bone, comprising a cerclage wire or thread, which is arranged for being tightened and fastened around the fractured bone, and at least one spacer, which is arranged on the cerclage wire or thread for maintaining the cerclage wire or thread at a certain distance from the fractured bone, wherein the at least one spacer is made as a band having a substantially rectangular plan and a concave profile, wherein the band has a pair of end walls, which are bent so as to extend in a direction opposite to the face of the band that, in use, is intended to be in contact with the surface of the fractured bone, and wherein each of the end walls is provided with a through-hole for the passage of the cerclage wire or thread, whereby the cerclage wire or thread is guided parallel to a longitudinal axis of the band, wherein the cerclage device further comprises at least one safety thread, wherein a single stop element is arranged on the safety thread, wherein each of the end walls of the band is correspondingly provided with at least one additional through-hole, wherein the safety thread passes through the respective additional through-holes of the end walls of the band and is guided parallel to the longitudinal axis of the band, whereby at least one of the end walls of the band is farther from an end of the safety thread than the stop element, and wherein the stop element has a size larger than the size of the additional through-holes of the end walls of the band.

2. The cerclage device according to claim 1, wherein the stop element is arranged at one end of the safety thread.

3. The cerclage device according to claim 1, wherein the stop element is arranged between the end walls of the band.

4. The cerclage device according to claim 1, wherein the face of the band that, in use, is intended to be in contact with the surface of the fractured bone has a smooth surface.

5. The cerclage device according to claim 1, wherein the face of the band that, in use, is intended to be in contact with the surface of the fractured bone is provided with projecting teeth.

6. The cerclage device according to claim 1, wherein the band comprises, in addition to the end walls, one or more intermediate walls, which extend in a direction opposite to the face of the band that, in use, is intended to be in contact with the surface of the fractured bone, each of the intermediate walls being provided with a through-hole for the passage of the cerclage wire or thread and with at least one additional through-hole for the passage of the at least one safety thread.

7. The cerclage device according to claim 1, wherein the band comprises a pair of bent tabs, which are arranged on the opposite lateral sides of the body of the band and extend in a direction opposite to the face of the band that, in use, is intended to be in contact with the surface of the fractured bone.

8. The cerclage device according to claim 1, wherein the band is preformed so as to have a desired concave profile.

9. The cerclage device according to claim 1, wherein the band is made of a deformable material and is adaptable to the profile of the fractured bone to which the cerclage device is applied.

10. The cerclage device according to claim 1, wherein the through-holes of the end walls of the band for the passage of the cerclage wire or thread are closed through-holes and have a circular profile.

11. The cerclage device according to claim 1, wherein one or more through-holes of the end walls of the band for the passage of the cerclage wire or thread are through-holes that are open toward a direction facing away from the face of the band that, in use, is intended to be in contact with the surface of the fractured bone.

12. The cerclage device according to claim 6, wherein the through-holes of the intermediate walls of the band for the passage of the cerclage wire or thread are closed through-holes and have a circular profile.

13. The cerclage device according to claim 6, wherein one or more of the through-holes of the intermediate walls of the band for the passage of the cerclage wire or thread are through-holes that are open toward a direction facing away from the face of the band that, in use, is intended to be in contact with the surface of the fractured bone.

14. A cerclage system for the cerclage of a fractured bone, which comprises an osteosynthesis plate and one or more cerclage devices according to claim 1.

15. A cerclage device for the cerclage of a fractured bone, comprising a cerclage wire or thread, which is arranged for being tightened and fastened around the fractured bone, and at least one spacer, which is arranged on the cerclage wire or thread for maintaining the cerclage wire or thread at a certain distance from the fractured bone, wherein the at least one spacer is made as a band having a substantially rectangular plan and a concave profile, wherein the band has a pair of end walls, which are bent so as to extend in a direction opposite to the face of the band that, in use, is intended to be in contact with the surface of the fractured bone, and wherein each of the end walls is provided with a through-hole for the passage of the cerclage wire or thread, whereby the cerclage wire or thread is guided parallel to a longitudinal axis of the band, wherein the cerclage device further comprises at least one safety thread, wherein a stop element is arranged on the safety thread, wherein each of the end walls of the band is correspondingly provided with at least one additional through-hole, wherein the safety thread passes through the respective additional through-holes of the end walls of the band and is guided parallel to the longitudinal axis of the band, whereby at least one of the end walls of the band is farther from an end of the safety thread than the stop element, wherein the stop element has a size larger than the size of the additional through-holes of the end walls of the band, and wherein the stop element is arranged between the end walls of the band.

16. The cerclage device according to claim 15, wherein the face of the band that, in use, is intended to be in contact with the surface of the fractured bone has a smooth surface or is provided with projecting teeth.

17. The cerclage device according to claim 15, wherein the band comprises, in addition to the end walls, one or more intermediate walls, which extend in a direction opposite to the face of the band that, in use, is intended to be in contact with the surface of the fractured bone, each of the intermediate walls being provided with a through-hole for the passage of the cerclage wire or thread and with at least one additional through-hole for the passage of the at least one safety thread.

18. The cerclage device according to claim 15, wherein the band comprises a pair of bent tabs, which are arranged on opposite lateral sides of the body of the band and extend in a direction opposite to the face of the band that, in use, is intended to be in contact with the surface of the fractured bone.

19. The cerclage device according to claim 15, wherein the band is preformed so as to have a desired concave profile.

20. The cerclage device according to claim 15, wherein the band is made of a deformable material and is adaptable to the profile of the fractured bone to which the cerclage device is applied.

* * * * *